United States Patent [19]

Castillo

[11] Patent Number: 4,826,001
[45] Date of Patent: May 2, 1989

[54] CONTACT LENS CASE

[75] Inventor: Bradley E. Castillo, Emeryville, Calif.

[73] Assignee: Barnes-Hind, Inc., Sunnyvale, Calif.

[21] Appl. No.: 179,799

[22] Filed: Apr. 11, 1988

[51] Int. Cl.⁴ .............................................. A45C 11/04
[52] U.S. Cl. .................................... 206/5.1; 206/205; 134/137; 422/301
[58] Field of Search ................... 206/5, 5.1, 6, 205; 134/137; 422/300, 301

[56] References Cited

U.S. PATENT DOCUMENTS

| | | | |
|---|---|---|---|
| 3,378,020 | 4/1968 | Grabiel | 206/5.1 |
| 3,379,200 | 4/1968 | Pennell | 206/5.1 |
| 3,623,492 | 11/1971 | Frantz | 134/143 |
| 3,997,049 | 12/1976 | Sherman | 206/5.1 |
| 4,002,234 | 1/1977 | Loshack | 206/205 |
| 4,009,777 | 3/1977 | Thomas | 206/5.1 |
| 4,011,941 | 3/1977 | Parsons | 206/5.1 |
| 4,200,187 | 4/1980 | Thomas | 206/5.1 |
| 4,396,583 | 2/1983 | LeBoeuf | 422/301 |

Primary Examiner—David T. Fidei
Attorney, Agent, or Firm—Burns, Doane, Swecker & Mathis

[57] ABSTRACT

A contact lens case is provided which includes a cannister open at its upper end for receiving lens washing fluid and a cap adapted to be secured to and seal the cannister. The cap includes a securing ring adapted to engage the cannister so as to secure the cap to the cannister. The cap further includes a lens retaining portion having at least two lens receptacles pivotably mounted on a shoulder. A leaf spring is provided in the shoulder for urging the lens receptacles apart. A turning knob is provided on the cap and is connected to a planetary gear mechanism for causing the lens retaining portion to rotate in the cannister as the turning knob is rotated. Downwardly extending finger means are provided on each lens receptacle which are adapted to engage an elliptically shaped track at the base of the inner surface of the cannister to cause the receptacles to be simultaneously oscillated toward and away from the axis of rotation of the retaining portion as the receptacle portion is rotated about the circumference of the cannister.

20 Claims, 3 Drawing Sheets

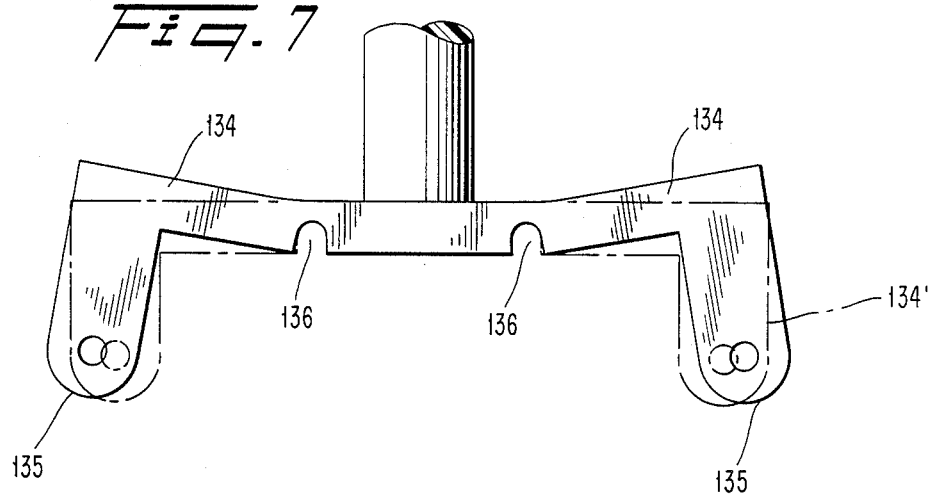
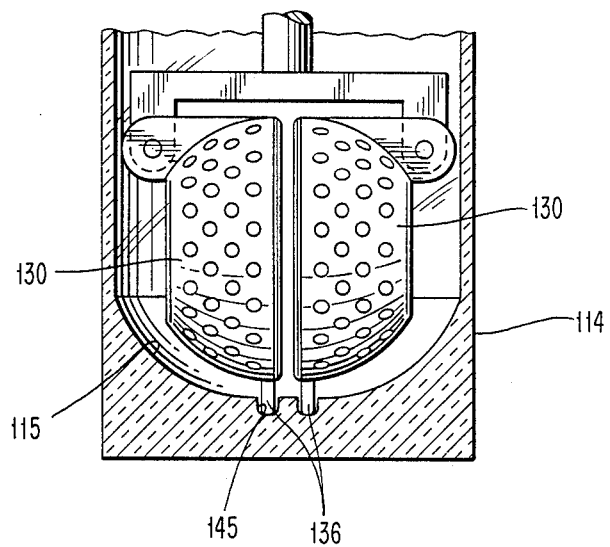
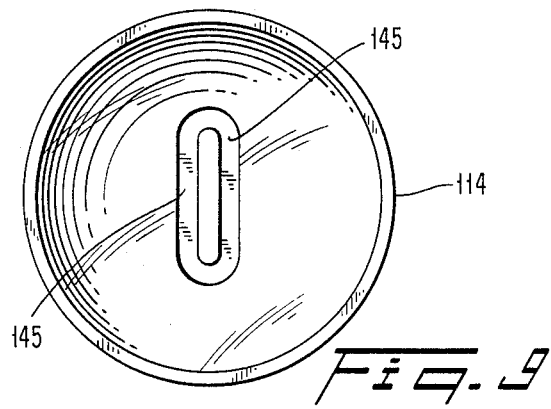

CONTACT LENS CASE

BACKGROUND OF THE INVENTION

I. Field of the Invention

The present invention relates generally to a contact lens case and, more particularly, to such a case which can be used to store both hard and soft contact lenses as well as to clean and rinse the lenses while in the case.

II. Description of the Prior Art

Both hard and soft contact lenses must be stored in enclosures or storage cases when not in use. Hard contact lenses should, preferably, be stored in an immersion fluid which acts to both clean the lenses and serves as an asepticizing agent to prevent the growth of undesirable organisms on the lens surfaces.

With soft contact lenses, there is even a greater requirement that the lenses be stored in an immersion fluid since such lenses are porous in nature and susceptible to drying out if not hydrated. Further, soft contact lenses must be periodically sterilized and cleaned to remove secretions from the eye and to prevent the growth of bacteria and the like on the lenses.

Sterilization of soft contact lenses is typically accomplished by immersion of the lenses in sterilizing chemicals or by heating the lenses while immersed in a saline solution. In direct contrast, lens cleaning may be accomplished either manually, i.e, physically rubbing the lenses with a cleaning fluid, or by insertion of the lenses into the type of contact lens storage case which includes mechanical cleaning means and then cleaning the lenses while in such a case.

One type of contact lens case having mechanical cleaning means is described, for example, in U.S. Pat. No. 3,623,492 which issued on Nov. 30, 1971 to D. G. Frantz for a Contact Lens Washer With Lens Storage. As described therein, a perforated basket for holding the lenses is provided within the contact lens storage case. The basket is attached to the lid of the case and a turn knob is provided to effect rotation of the basket around the case. As the basket is rotated, the cleaning solution contained within the case is agitated and is drawn through the perforations of the basket, thus enhancing the cleaning of the lenses.

Similarly, U.S. Pat. No. 3,997,049, which issued on Dec. 14, 1976 to G. J. Sherman, teaches an Enclosure For Hard And Soft Contact Lenses which includes a pair of lens retaining baskets contained within an enclosure. The baskets are pivotably mounted to the cap of the container so that when the cap is removed from the enclosure, the baskets may be folded outwardly to allow unimpaired access to the lenses in the baskets, and when the cap is secured on the enclosure, the baskets can rotate within the enclosure causing agitation of the fluid to enhance cleaning of the lenses in the baskets.

In each of the above cases or enclosures, the baskets are rotated in a single rotational plane around the case and the resultant agitation serves to enhance cleaning of the lenses. While such agitation effectively removes normal eye secretions and the like from the lenses, it is not particularly effective in removing more resistant residues. It has been found, however, that if the baskets are simultaneously moved in multiple planes, i.e, in a rotational direction around the circumference of the case as well as oscillated in a direction toward and away from their axis of rotation, the agitation of the cleaning or washing solution is substantially increased with an attendant increase in lens cleaning.

Against the foregoing background, it is a primary object of the present invention to provide a storage case for storing contact lenses in perforated lens receptacles suspended within the case.

It is another object of the present invention to provide such a contact lens case which permits cleaning or rinsing of the lenses while being stored in the case.

It is still another object of the present invention to provide such a contact lens case which can be used to store and clean both hard and soft contact lenses.

It is yet still another object of the present invention to provide such a contact lens case which includes a pair of perforated basket-type lens receptacles adapted to readily receive the lens.

It is still yet another object of the present invention to provide such a contact lens case in which the perforated lens receptacles containing the contact lenses may be rotated about the circumference of the case while the individual lens receptacles are simultaneously oscillated toward and away from the axis of rotation of the receptacles.

SUMMARY OF THE INVENTION

To the accomplishments of the foregoing objects and advantages, the present invention, in brief summary, comprises a contact lens case which includes a cannister open at its upper end for receiving lens contact lens rinsing or cleansing fluid and a cap adapted to be secured to and seal the cannister. The cap includes a securing ring which is adapted to engage complementary securing means on the cannister.

The cap of the contact lens case further includes a lens retaining portion having at least two lens receptacles pivotably mounted on a shoulder. A leaf spring is provided in the shoulder for urging the lens receptacles apart. The cap further includes a turning knob which is connected to a planetary gear mechanism for causing the lens retaining portion to rotate in the canister as the turning knob on the cap is rotated. Downwardly extending finger means are provided on each lens receptacle and are adapted to engage a complementary, elliptically shaped, track at the base of the inner surface of the canister to cause the lens receptacles to be simultaneously oscillated toward and away from the axis of rotation of the lens retaining portion as the lens receptacle portion is rotated about the circumference of the cannister.

BRIEF DESCRIPTION OF THE DRAWINGS

The foregoing and still other objects and advantages of the present invention will be more apparent from the following detailed explanation of the preferred embodiments of the invention in connection with the accompanying drawings wherein:

FIG. 7 illustrates an alternative embodiment of the lens retaining portion without a leaf spring being provided therein;

FIG. 8 is a side view of an alternative embodiment of the lens case of the present invention; and FIG. 9 is a top view of the cannister of the embodiment of FIG. 9.

DESCRIPTION OF THE PREFERRED EMBODIMENTS

Figure 1:
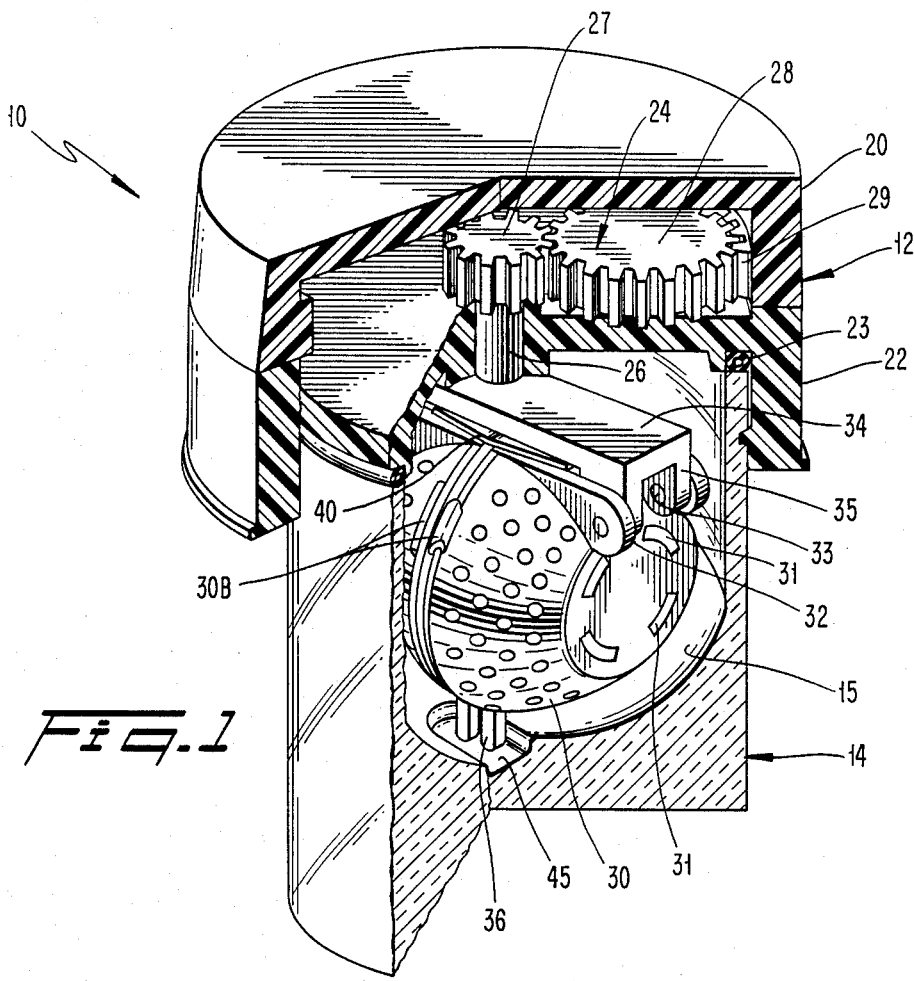
FIG. 1 is a cutaway, perspective illustration of the contact lens case of the present invention.

The contact lens case of the present invention, referred to generally by reference numeral 10, includes a cap 12 adapted to threadably engage and seal with a cannister 14 to form the case 10. As shown in FIG. 1, the cap 12 includes an internally threaded, securing ring 22 which is adapted to engage complementary external threads on the upper portion of the cannister 14 to secure and seal the cap 12 to the cannister 14. A gasket 23 is provided in the securing ring 22 for securely sealing the cap 12 to the cannister 14 to prevent contact lens washing or rinsing fluid from leaking from the case 10 during use.

A turning knob 20 is provided on the cap 12 and is adapted to be rotatably mounted relative to the securing ring 22. Through a planetary gear mechanism 24, the turning knob 20 is adapted to transfer its rotary motion to a lens retaining portion 25 which includes a pair of perforated, basket-type, lens receptacles 30, each of which is adapted to receive and store a contact lens.

The planetary gear mechanism 24 is similar to the mechanism described in U.S. Pat. No. 3,623,492, the disclosure of which is hereby incorporated herein by reference. Internal teeth 29 are provided on the inner surface of the turning knob 20 and are adapted to engage and cause to rotate a planetary gear 28 which is, likewise, adapted to engage and cause to rotate a spur gear 27 which is attached to the upper end of a trunnion rod 26. A lens retaining portion 25 including a pair of perforated basket-type, lens receptacles 30 is mounted on the opposite end of the trunnion rod 26 and is suspended within the case lo when the cap 12 is secured to the cannister 14. Thus, as the turning knob 20 is rotated relative to the securing ring 22, the planetary gear mechanism 24 causes the lens retaining portion 25 suspended within the cannister 14 to correspondingly rotate about the cannister 14.

Figure 2:
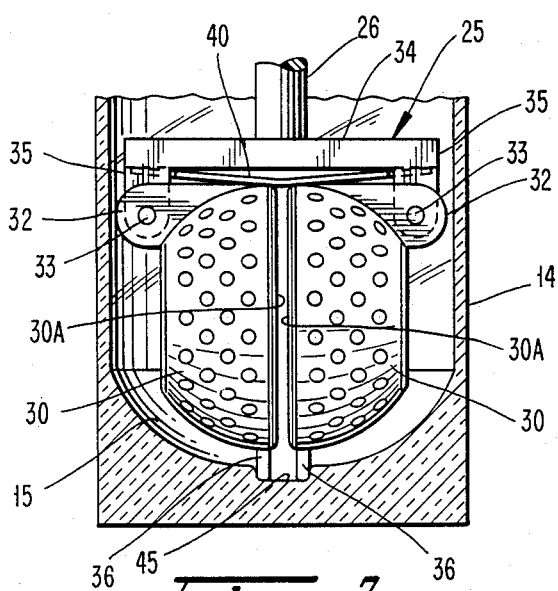
FIG. 2 is a side view of the lens retaining portion of the contact lens case with the lens receptacles shown in a closed position.
Figure 3:
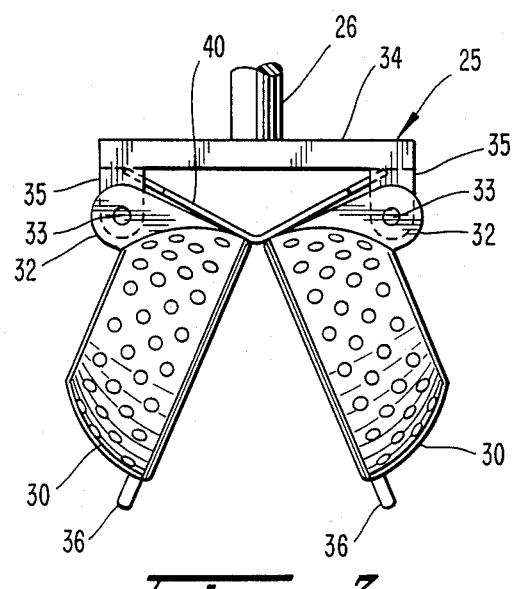
FIG. 3 is a side view of the lens retaining portion with the lens receptacles in an open position.

The lens retaining portion 25, which is shown in greater detail in FIGS. 2 and 3, is attached to the trunnion rod 26 by a shoulder 34 which includes a pair of opposed, downwardly extending, hinge arms 35. Each of the pair of foraminous or perforated, basket-type, lens receptacles 30 has a hinge element 32 which is pivotably mounted at pivot point 33 to a complementary hinge arm 35 on the shoulder 34. Each of the lens receptacles 30 includes a pair of perforated covers 30A adapted to receive and positively retain therein at least one contact lens and latch means 30B for securing the perforated covers 30A to the lens receptacles 30. Each lens receptacle 30 and the pair of covers 30A for each receptacle 30 is similar to the receptacles or baskets described in U.S. Pat. No. 3,997,049, the disclosure of which is hereby incorporated by reference thereto, in that the pair of covers can be contoured so that one has a generally convex body and the other has a planar body thereby forming a composite structure having a generally spherical shape adapted to receive a complementary configured contact lens. Further, the lens receptacles 30 are adapted to fold toward and away from each other when the lens is removed from the receptacle 30 to allow easy access to the lens in each receptacle 30.

Figure 6:
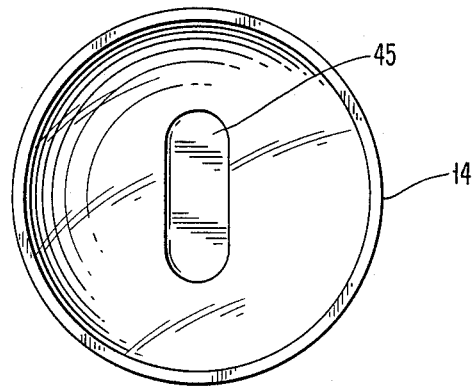
FIG. 6 is a top view of the cannister of the lens case illustrating the configuration of the track provided at the base of the inner surface of the cannister.

Unlike any of the devices in the prior art, a finger 36 is provided at the lower end of each lens receptacle 30. The finger 36 may be integrally formed with the respective lens receptacle 30 or it may be a plastic or metal finger or a clip which is secured to the lens receptacles 30. The fingers 36 preferably extended outwardly from the covers 30A. The fingers 36 are adapted to be inserted into and travel within a predefined track 45 provided at the base of the inner surface or wall 15 of the cannister 14. The track 45, as shown in FIG. 6, may be elliptical or spherical in shape.

Figure 4:
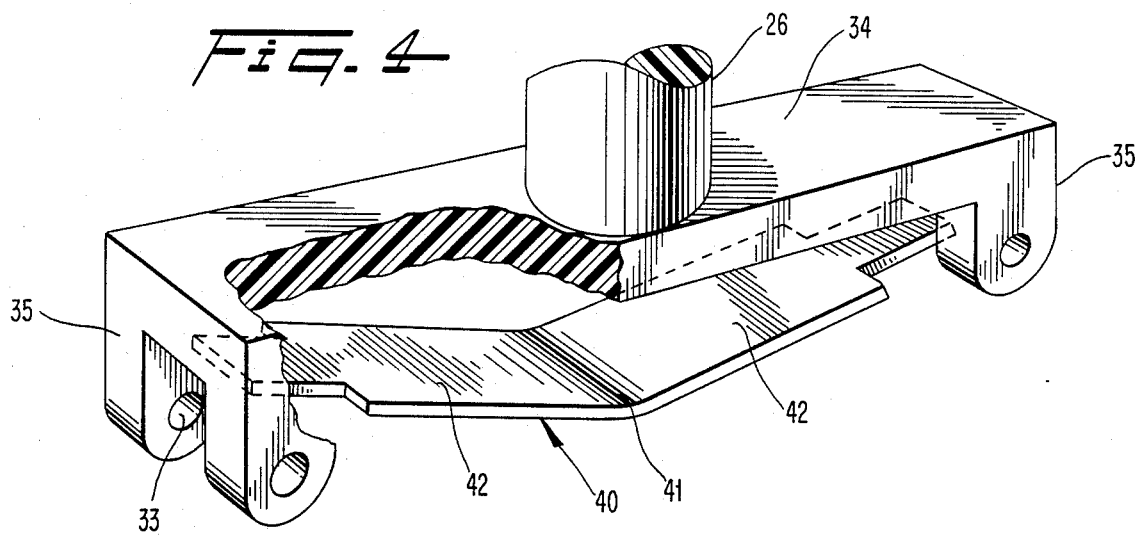
FIG. 4 is an enlarged perspective view of the lens retaining portion of the present invention.
Figure 5:
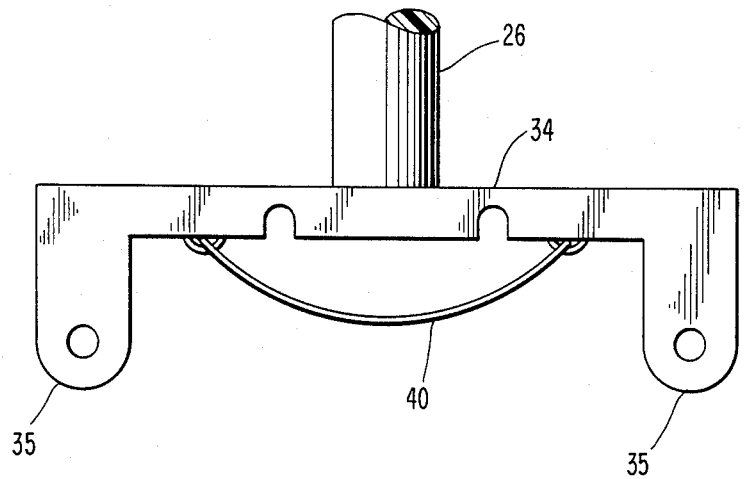
FIG. 5 is an enlarged front view of the lens retaining portion illustrating the spring bias action of the leaf spring therein.

As shown in FIGS. 4 and 5, a leaf spring 40 is provided between the hinge arms 35 of the shoulder 34. The leaf spring 40 has a bend in its center portion 41 so that the legs 42 of the spring 40 biases in a downward direction with respect to the shoulder 34. The leaf spring 40 is adapted to apply downward pressure against the lens receptacles 30, thus serving to urge the finger 36 of each receptacle 30 shown in FIG. 3 against the outer edge or circumference of the track 45 provided at the base of the inner surface 15 of the cannister 14 shown in FIG. 6 thereby permitting lens receptacles 30 to oscillate as the turning knob 20 is turned. As shown in FIG. 3, the leaf spring 45 also serves to urge the lens receptacles 30 apart when the lens retaining portion 25 is removed from the cannister 14 to facilitate access to the contact lenses being stored therein.

As illustrated in FIG. 7, the hinge arms 135 of the shoulder 134 may, in an alternative embodiment, be modified by pre-casting the arms 135 with a slight upward curve. Cut-outs 136 permit the hinge arms 135 and shoulder 134 to be able to deflect or bend, thus eliminating the need for the incorporation of a leaf spring 40 as provided in the embodiment of FIG. 5. In this embodiment, when two receptacles are urged into cannister 14, the cannister forces the two receptacles together so that shoulder 134 is at cut-outs 136 bent downward from its curved, natural position to a horizontal position as shown by dotted lines 134' in FIG. 7, and further, the finger 36 of each receptacle 30 enter into predefined track 45 provided at the bas of cannister 14 as shown in FIG. 2. The natural bias of shoulder 134 causes it to revert back to its curved or bowed position so as to provide the force that causes the finger 36 of each receptacle 30 to follow the predefined track 45 provided at the base of the inner surface 15 of the cannister 14.

It will be appreciated that the lens case 10 operates in the following manner. The lens case 10 is opened by disengaging the securing ring 22 from the cannister 14 thus permitting access to the lens retaining portion 25. The leaf spring 40 urges the individual lens receptacles 30 apart to facilitate access to the individual receptacles and to permit contact lenses to be introduced into the proper receptacle 30. The lenses are retained in the lens receptacles 30 by engaging the respective covers 30A to the receptacles 30 by latch means 30B. Lens cleaning or rinsing fluid is then added to the cannister 14 and the cap 12 is re-secured to the cannister 14 by engaging securing ring 22. When the cap 12 re-engages the cannister 14, the fingers 36 at the bottom of the lens receptacles 30 are urged by the action of leaf spring 40 into the track 45 at the base of the inner surface 15 of the cannister 14.

Cleaning or rinsing of the contact lenses contained within the lens receptacles 30 is effected by rotation of the turning knob 20 which causes the lens retaining portion 25 including the lens receptacles 30 to rotate about the cannister 14. The lens receptacles 30 are simultaneously oscillated toward and away from one another and their normal axis of rotation as the lens receptacles 30 rotate about the cannister 14 and as the fingers 36 travel within the oval track 45, due to the following factors: the retention of the fingers 36 within the track 45 at the base of the inner surface 15 of the cannister 14, the elliptical or oval shape of the track 45, and the action of the leaf spring 40 which biases the fingers 36 in an outward direction. It will be appreciated that when the fingers ar at the narrowest portion of the track 45 the individual lens receptacles 30 are urged together. Similarly, when the fingers 36 are positioned at the widest portion of the track 45, the lens receptacles 30 are permitted to spread apart.

As the lens receptacles 30 are so rotated and oscillated, the cleaning or rinsing fluid becomes agitated and is forced through the perforations in the lens receptacles 30. This action effects a thorough cleaning of the contact lenses captured therein due to the fact that fluid is forced against the from and back surfaces of the lenses.

FIGS. 8-9 illustrate an alternative embodiment in which track 145 is provided on the base of the inner surface 115 of a cannister 114. The lens receptacles 130 are simultaneously oscillated toward and away from one another and their normal axis of rotation as the fingers 136 travel within the track 145. As shown in FIG. 9, the track 145 is only sufficiently wide to accommodate the finger 136 and, as such, oscillation is accomplished as the fingers 136 travel around track 145. In such an embodiment, there is no necessity for a leaf spring 40 as used in the embodiment of FIGS. 1-6 to urge the fingers against the outer edges of the track 45.

It will be appreciated that the fingers 136 of the embodiment of FIGS. 8-9 can be spring loaded to simultaneously force the individual lens receptacles 130 together as they travel about the track 145.

Having thus described the invention with particular reference to the preferred forms thereof, it will be obvious that various changes and modifications may be made therein without departing from the spirit and scope of the invention as defined by the appended claims.

Wherefore, I claim:

1. A contact lens case including:
 a cannister, open at its top end, for receiving contact lens fluid; and
 a cap including:
  a securing ring for securing the cap to said cannister;
  a lens retaining portion including at least two perforated lens receptacles, each adapted to receive and store a contact lens;
  rotational means for causing the lens retaining portion to rotate within said cannister about an axis of rotation; and
  oscillating means for causing each of said lens receptacles to be oscillated toward and away from the axis of rotation of said lens retaining portion as said lens retaining portion is rotated about said axis of rotation within said cannister.

2. The contact lens case of claim 1, wherein said cannister includes threads at a point proximately spaced from its top end and said securing ring includes internal threads complementary to the threads on said cannister, and wherein said securing ring is adapted to engage the threads on said cannister for securing said cap to said cannister.

3. The contact lens case of claim 2, wherein said cap further includes a gasket for sealing said cap to said cannister.

4. The contact lens case of claim 1, wherein said lens receptacles are perforated, basket-type receptacles.

5. The contact lens case of claim 1, wherein said lens receptacles each include a cover and latch means for securing said cover so as to positively secure a contact lens therein.

6. The contact lens case of claim 1, wherein said lens receptacles are pivotably mounted on a shoulder portion of said lens retaining portion.

7. The contact lens case of claim 6, wherein said lens receptacles are biased in a direction perpendicular to said axis of rotation by a leaf spring provided in said shoulder portion.

8. The contact lens case of claim 7, wherein said leaf spring has a bend in its center portion so as to bias the legs of said leaf spring in the direction opposite from said shoulder portion.

9. The contact lens case of claim 6, wherein said shoulder portion has a gradual upward curve with at least one cutout portion therein so as to provide a spring bias in the direction opposite from said shoulder portion.

10. The contact lens case of claim 1, wherein said rotational means comprises a turning knob provided on said cap and a planetary gear mechanism connected to said cap.

11. The contact lens case of claim 10, further including a trunnion rod connected to said lens retaining portion, wherein said planetary gear mechanism is adapted to transfer the rotation of said turning knob to said trunnion rod.

12. The contact lens case of claim 10, wherein said planetary gear mechanism constitution internal teeth provided on the inner surface of said turning knob, a planetary gear adapted to engage said internal teeth, and a spur gear attached to said trunnion rod which is adapted to engage said planetary gear.

13. The contact lens case of claim 1, wherein said oscillating means comprises at least one downwardly extending finger member connected to each lens receptacle, wherein said cannister has an elliptically shaped track at the base of the inner portion thereof, and wherein said finger member is adapted to engage and travel within said track.

14. The contact lens case of claim 13, wherein said finger member is spring biased so as to engage said track.

15. A contact lens case including:
 a cannister, open at its top, for receiving contact lens fluid; and
 a cap including:
  a securing ring adapted to secure said cap to said cannister;
  a lens retaining portion including at least two lens foraminous receptacles, each of said lens receptacles being adapted to receive and store a contact lens;

transfer means connected to said lens retaining portions;

a turning knob provided on said cap and a planetary gear mechanism connected to said cap, said planetary gear mechanism being adapted to transfer by said transfer means the rotation of said turning knob to said lens retaining portion for causing said lens retaining portion to rotate about an axis of rotation in said cannister; and oscillating means for causing each of said lens receptacles to be simultaneously oscillated toward and away from the axis of rotation of said lens receptacle portion as said lens retaining portion is rotated within said cannister.

16. The contact lens case of claim 15, wherein said oscillating means comprises at least one finger member extending downwardly from each of said lens receptacles, wherein said cannister has an elliptically shaped track in the base of the inner portion thereof, and wherein said at least one finger member is adapted to engage and travel within said track.

17. The contact lens case of claim 15, wherein said transfer means is a trunnion.

18. A contact lens case including:

a cannister, open at its top, for receiving lens washing fluid, and having an elliptically shaped track in the base of the inner portion thereof; and a cap including:

a securing ring adapted to threadably engage said cannister so as to secure said cap to said cannister;

a lens retaining portion including at least two lens receptacles pivotably mounted on a shoulder, said shoulder including a spring for biasing said lens receptacles in a direction away from said shoulder;

a turning knob provided on said cap and a planetary gear mechanism connected to said cap, said planetary gear mechanism being adapted to cause said lens retaining portion to rotate as said turning knob is rotated and oscillating means comprising at least one finger member extending downwardly from each of said lens receptacles, said finger members being adapted to engage and travel within said elliptically shaped track in said cannister, wherein said oscillating means causes each of the lens receptacles to be oscillated toward and away from the axis of rotation of said lens retaining portion as said lens retaining portion is simultaneously rotated about the circumference of said cannister.

19. A contact lens case including:

a cannister, open at its top, for receiving lens washing fluid, and having a pre-defined pathway in the base of the inner portion thereof; and a cap including:

a securing ring adapted to threadably engage said cannister so as to secure said cap to said cannister;

a lens retaining portion including at least two lens receptacles pivotably mounted on a shoulder, a turning knob provided on said cap and a planetary gear mechanism connected to said cap, said planetary gear mechanism being adapted to cause said lens retaining portion to rotate as said turning knob is rotated; and oscillating means comprising at least one finger member extending downwardly from each of said lens receptacles, said finger members being adapted to engage and travel within said pathway in said cannister, wherein said oscillating means causes each of the lens receptacles to be oscillated toward and away from the axis of rotation of said lens retaining portion as said lens retaining portion is simultaneously rotated about the circumference of said cannister.

20. A contact lens case including:

a cannister, open at its top, for receiving lens washing fluid, and having a track in the base of the inner portion thereof; and a cap including:

a securing ring adapted to threadably engage said cannister so as to secure said cap to said cannister;

a lens retaining portion including at least two lens receptacles pivotably mounted on a shoulder, a turning knob provided on said cap and a planetary gear mechanism connected to said cap, said planetary gear mechanism being adapted to cause said lens retaining portion to rotate as said turning knob is rotated; and oscillating means comprising at least one finger member extending downwardly from each of said lens receptacles and means for spring biasing said lens receptacles toward one another and said finger members into said track, wherein said oscillating means causes each of the lens receptacles to be oscillated toward and away from the axis of rotation of said lens retaining portion as said lens retaining portion is simultaneously rotated about the circumference of said cannister.

* * * * *